(12) United States Patent
Robinson et al.

(10) Patent No.: US 8,192,929 B2
(45) Date of Patent: Jun. 5, 2012

(54) ASSAY SYSTEM FOR MONITORING THE EFFECTS OF GENETICALLY ENGINEERED CELLS TO ALTER FUNCTION OF A SYNCTIUM

(75) Inventors: Richard B. Robinson, Cresskill, NJ (US); Michael R. Rosen, Manhattan, NY (US); Ira S. Cohen, Stony Brook, NY (US); Peter R. Brink, Setauket, NY (US)

(73) Assignees: The Trustees of Columbia University in the City of New York, New York, NY (US); The Research Foundation of State University of New York, Albany, NY (US)

( * ) Notice: Subject to any disclaimer, the term of this patent is extended or adjusted under 35 U.S.C. 154(b) by 778 days.

(21) Appl. No.: 11/792,426

(22) PCT Filed: Jul. 19, 2005

(86) PCT No.: PCT/US2005/025735
§ 371 (c)(1),
(2), (4) Date: Nov. 24, 2009

(87) PCT Pub. No.: WO2006/020322
PCT Pub. Date: Feb. 23, 2006

(65) Prior Publication Data
US 2010/0068699 A1    Mar. 18, 2010
US 2012/0028241 A2    Feb. 2, 2012

Related U.S. Application Data

(60) Provisional application No. 60/589,416, filed on Jul. 19, 2004.

(51) Int. Cl.
C12Q 1/68 (2006.01)
C12N 5/00 (2006.01)
(52) U.S. Cl. .......................................... 435/6.1; 435/325
(58) Field of Classification Search .................... 435/6.1, 435/325
See application file for complete search history.

(56) References Cited

U.S. PATENT DOCUMENTS

| 6,387,369 B1 * | 5/2002 | Pittenger et al. ............. 424/93.7 |
| 6,410,236 B1 * | 6/2002 | Metzger ............................. 435/6 |
| 6,776,987 B1 * | 8/2004 | Edelberg et al. ........... 424/93.21 |
| 2002/0155101 A1 | 10/2002 | Donahue et al. |
| 2003/0082153 A1 | 5/2003 | Epstein et al. |

FOREIGN PATENT DOCUMENTS

WO    WO 02075302 A1    9/2002

OTHER PUBLICATIONS

Qu et al. Circulation 107:1106-1109, 2003.*
Miake, J. et al. "Gene therapy: biological pacemaker created by gene transfer." Nature 419: 132-133 Sep. 12, 2002.
Miake, J. et al "Functional role of inward rectifier current in heart probed by Kir2.I overexpression and dominant-negative suppression." J. Clinical. Investigation 111 (10): 1529-36, May 2003.

* cited by examiner

*Primary Examiner* — Marcia S Noble
(74) *Attorney, Agent, or Firm* — Evans & Molinelli PLLC; Judith A. Evans

(57) ABSTRACT

This invention provides methods for determining the ability of a gene construct to alter the rhythm and contractility of a syncytial cell. Furthermore, this invention provides methods for constructing a gene construct capable of altering the rhythm or contractility of a syncytial cell. Finally, this invention provides a method for constructing a gene construct capable of coupling to a syncytial cell.

26 Claims, 8 Drawing Sheets

A

B

C

△ WHITE = STEM TO STEM
△ STRIPE = STEM TO MYOCARDIUM
△ DOTS = INTERCALATED DISC

US 8,192,929 B2

ASSAY SYSTEM FOR MONITORING THE EFFECTS OF GENETICALLY ENGINEERED CELLS TO ALTER FUNCTION OF A SYNCTIUM

This application is the national phase application of PCT Application No. PCT/US2005/025735, filed Jul. 19, 2005, which claims the benefit of U.S. Provisional Application No. 60/589,416, filed Jul. 19, 2004, the entire contents of which are hereby incorporated into this application by reference.

Throughout this application, various publications are referenced to by numbers. Full citations may be found at the end of the specification immediately preceding the claims. The disclosures of these publications in the entireties are hereby incorporated by reference into this application in order to more fully describe the state of the art to those skilled therein as of the date of the invention described and claimed herein.

This invention was made with support under United States Government NIG NHLBI Grant No. HL-28958. Accordingly, the U.S. Government has certain rights in this invention.

BACKGROUND OF THE INVENTION

Although electronic pacemakers are currently the mainstay of therapy for heart block and other electrophysiological abnormalities, they are not optimal. Among their shortcomings are limited battery life, the need for permanent catheter implantation into the heart, and lack of response to autonomic neurohumors. (1) For these reasons, several gene therapy approaches have been explored as potential alternatives. These include either overexpression of $\beta_2$-adrenergic receptors (2, 3) use of a dominant-negative construct to suppress inward rectifier current when expressed together with the wild-type gene Kir2.1 (4) and implantation of vectors carrying the pacemaker gene, HCN2, into atrium (5) or bundle branch system. (6) A problem inherent in some of these approaches (2-6) is the use of viruses to deliver the necessary genes. Although the vectors have been replication-deficient adenoviruses that have little infectious potential, these incorporate the possibility of only a transient improvement in pacemaker function as well as potential inflammatory responses. The use of retroviruses and other vectors, although not attempted as yet for biological pacemakers, carries a risk of carcinogenicity and infectivity that is unjustified, given the current success of electronic pacemakers. Attempts to use embryonic human stem cells to create pacemakers are still in their infancy and carry the problems of identifying appropriate cell lineages, the possibility of differentiation into lines other than pacemaker cells, and potential for neoplasia (see overview (7)).

SUMMARY OF THE INVENTION

This invention provides a method for determining the ability of a gene construct to alter the rhythm of a syncytial cell comprising: (i) contacting the gene construct to a syncytial cell; and (ii) determining whether the rhythm in the contacted syncytial cell is different than that in a syncytial cell to which the gene construct was not contacted, thereby determining whether the gene construct alters the rhythm of the syncytial cell.

This invention further provides a method for determining the ability of a gene construct to alter contractility of a syncytial cell comprising: (i) contacting the gene construct to the syncytial cell; and (ii) determining whether the contractility in the contacted syncytial cell is different than that in a syncytial cell to which the gene construct was not contacted, thereby determining whether the gene construct alters the contractility of the syncytial cell.

This invention further provides a method of determining the coupling of a gene construct to a syncytial cell, comprising, (a) contacting the gene construct to the syncytial cell, in vitro; (b) determining the rhythm of the contacted syncytial cell; and (c) comparing the rhythm so determined with the rhythm of the same syncytial cell prior to the contacting of the gene construct, the coupling of the gene construct to the syncytial cell being indicated when the rhythm of the contacted syncytial cell is different than the rhythm of the same syncytial cell prior to the contacting of the gene construct was not contacted.

This invention further provides a method for producing a gene construct capable of altering the rhythm of a syncytial cell comprising the steps of (a) contacting a cell, known to have the ability to couple to a syncytial cell, with a gene to form a gene construct; (b) contacting the gene construct of step (a) to a syncytial cell, in vitro; (c) determining the rhythm of the contacted syncytial cell; (d) comparing the rhythm so determined with the rhythm of the same syncytial cell prior to the contacting of the gene construct, the gene construct's ability to alter the rhythm of the syncytial cell being indicated when the rhythm of the contacted syncytial cell is different than the rhythm of the same syncytial cell prior to the contacting of the gene construct; and (e) selecting the gene construct of step (d) which is determined to have the ability to alter the rhythm of the syncytial cell.

This invention further provides a method for producing a gene construct capable of altering the contractility of a syncytial cell comprising the steps of (a) contacting a cell, known to have the ability to couple to a syncytial cell, with a gene to form a gene construct; (b) contacting the gene construct of step (a) to a syncytial cell, in vitro; (c) determining the contractility of the contacted syncytial cell; (d) comparing the contractility so determined with the contractility of the same syncytial cell prior to contacting of the gene construct, the gene construct's ability to alter the contractility of the syncytial cell being indicated when the contractility of the contacted syncytial cell is different than the contractility of the same syncytial cell prior to the contacting of the gene construct; and (e) selecting the gene construct of step (d) which is determined to have the ability to alter the contractility of the syncytial cell.

Finally, this invention provides a method for producing a gene construct capable of coupling to a syncytial cell comprising the steps of (a) contacting a cell, known to have the ability to couple to a syncytial cell, with a gene to form a gene construct; (b) contacting the gene construct of step (a) to a syncytial cell, in vitro; (c) determining the rhythm of the contacted syncytial cell; (d) comparing the rhythm so determined with the rhythm of the same syncytial cell prior to the contacting of the gene construct, the coupling of the gene construct to the syncytial cell being indicated when the rhythm of the contacted syncytial cell is different than the rhythm of the same syncytial cell prior to the contacting of the gene construct; and (e) selecting the gene construct of step (d) which is determined to have coupled with the syncytial cell.

$I_f$ was expressed in hMSCs transfected with the mHCN2 gene (B) but not in nontransfected stem cells (A). (C) Fit by the Boltzmann equation to the normalized tail currents of $I_f$ gives a midpoint of $-91.8\pm0.9$ mV and a slope of $8.8\pm0.5$ mV (n=9). $I_f$ was fully activated around −140 mV with an activation threshold of −60 mV. Inset shows representative tail currents used to construct $I_f$ activation curves. Voltage protocol was to hold at −30 mV and hyperpolarize for 1.5 seconds to voltages between −40 and −160 mV in 10-mV increments followed by a 1.5-second voltage step to +20 mV to record the tail currents.

FIGS. 2A-2D Effect of extracellular application of $Cs^+$ and measurement of the reversal potential of $I_f$.

$I_f$ was recorded before (A), during (B), and after (C) external addition of 4 mmol/L $Cs^+$. (D) Fully activated I-V relationship of $I_f$ in the absence and presence of $Cs^+$. Voltage protocol was to hold at −30 mV and hyperpolarize to −150 mV for 2 seconds followed by a 1.5-second depolarization to voltages between −150 and +20 mV to record the tail currents necessary to construct the fully activated current-voltage relation followed by a 0.5-second step to −10 mV.

FIGS. 3A-3D Modulation of $I_f$ activation by isoproterenol (ISO) in hMSCs transfected with the mHCN2 gene.

Figure 1:
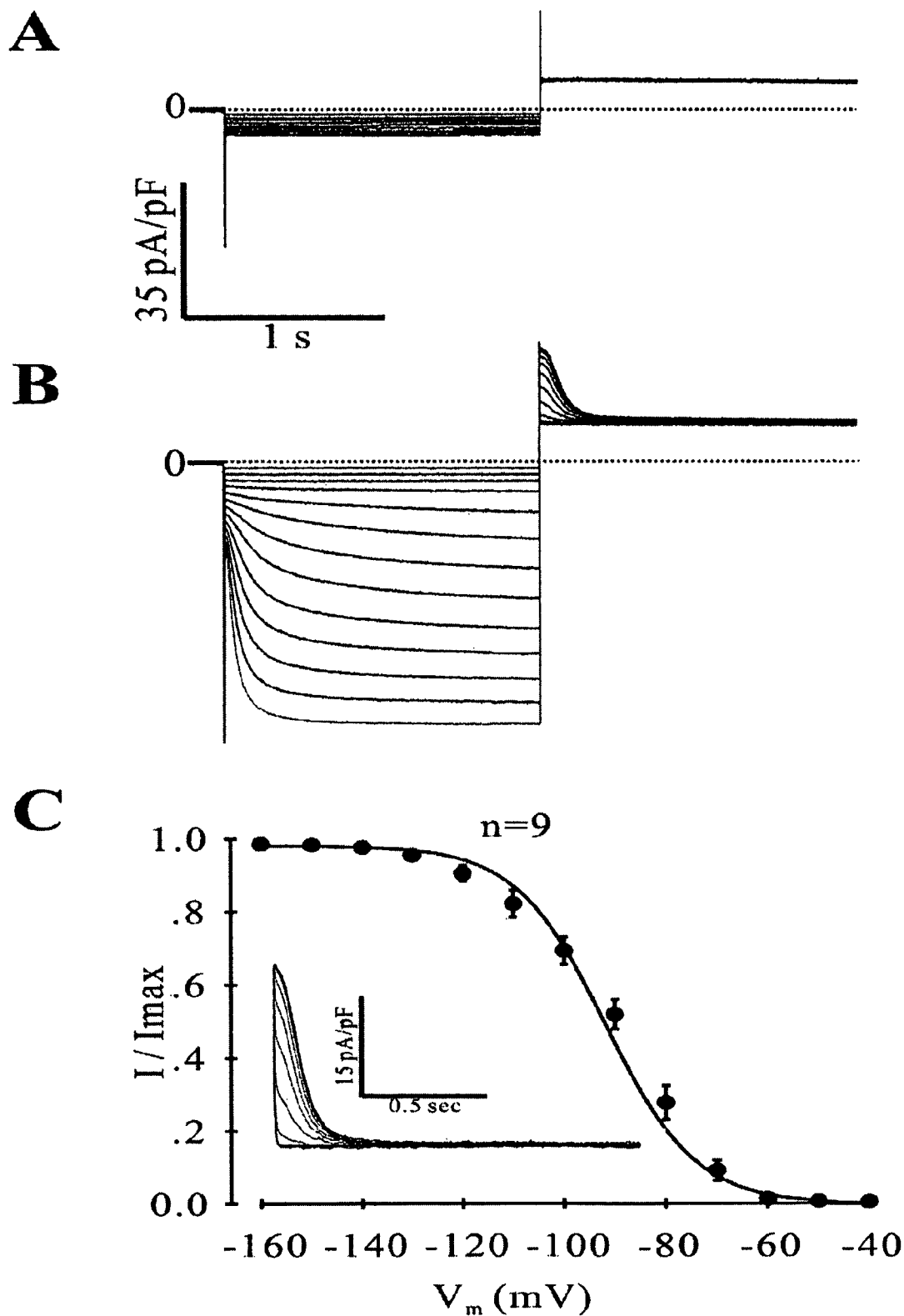
FIGS. 1A-1C Functional expression of $I_f$ in hMSCs transfected with mHCN2 gene.
Figure 2:
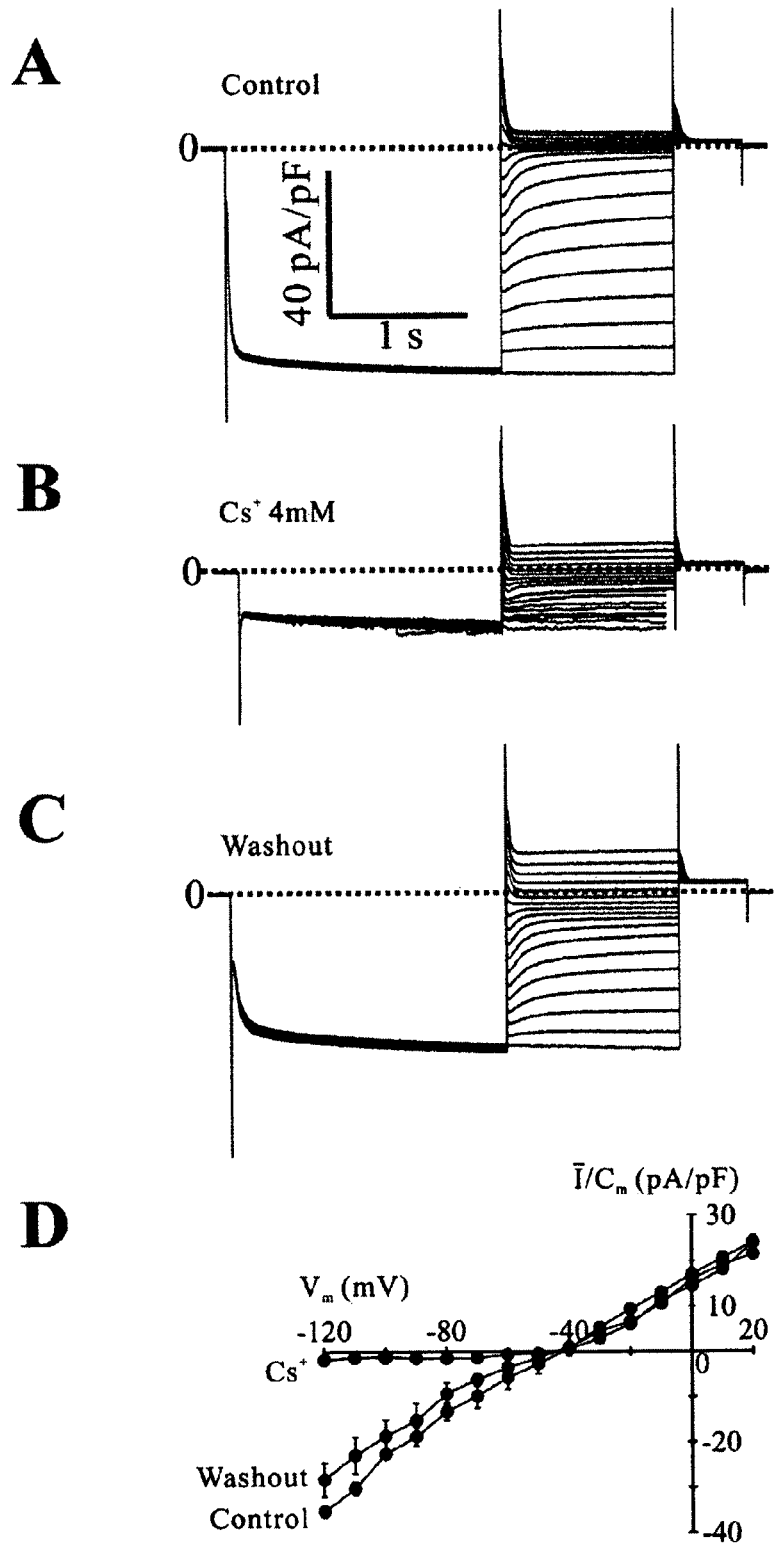

$I_f$ activation in the absence (A) and presence of ISO, $1 \times 10^{-6}$ mol/L (B). (C) Voltage dependence of activation of $I_f$ in control, ISO, and washout using a two-step pulse protocol. (D) Boltzmann fit to the normalized density of tail currents. Activation curve was constructed with the same protocol as in FIG. 1. Two-pulse protocol was initiated from a holding potential of −30 mV. First step was to −100 mV for 1.5 seconds followed by a second step to −150 mV for 1 second. Voltage was then stepped to +15 mV for 1 second to rapidly deactivate the current and then returned to the holding potential.

FIGS. 4A-4D Modulation of $I_f$ activation by acetylcholine (ACh) in the presence of ISO.

$I_f$ activation in the presence of ISO and in the absence (A) and presence (B) of ACh ($1 \times 10^{-6}$ mol/L). (C) Same two-step protocol as in FIG. 3C, for ISO ($1 \times 10^{-6}$ mol/L) alone and ISO+ACh. (D) Boltzmann fit to normalized currents. Activation curve was constructed with the same protocol as in FIG. 1.

FIGS. 5A-5B Pacemaker function in in vitro model.

Spontaneous electrical activity of neonatal rat ventricular myocytes cocultured for 4 to 5 days with hMSCs transfected with EGFP alone (A) or mHCN2 and EGFP (B). Experiments were conducted at 35° C.

Figure 6:
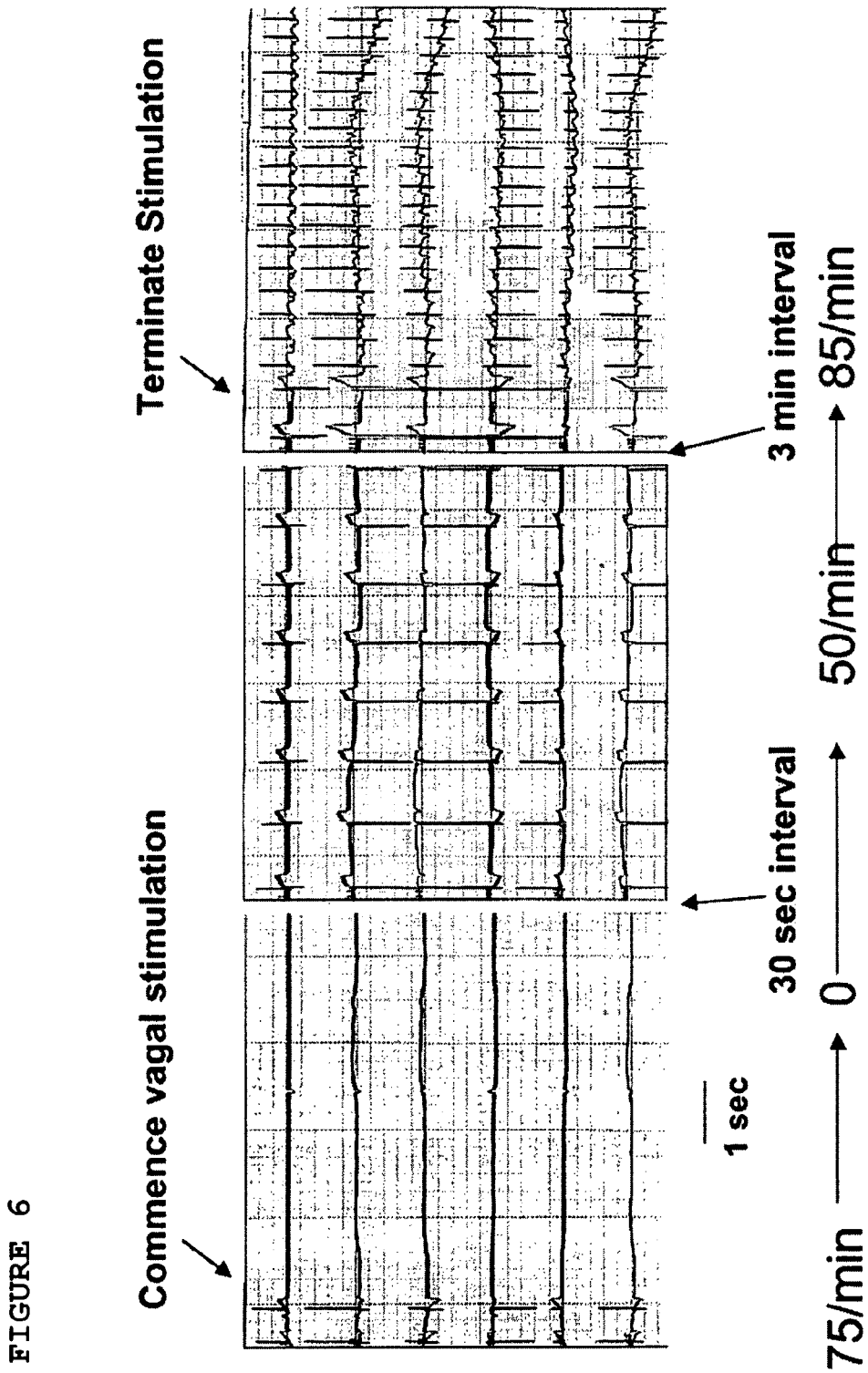

FIG. 6 Pacemaker function in canine heart in situ.

Top to bottom, ECG leads I, II, III, AVR, AVL, and AVF. Left, Last two beats in sinus rhythm and onset of vagal stimulation (arrow) causing sinus arrest in a dog studied 7 days after implanting mHCN2-transfected hMSCs in LV anterior wall epicardium. Middle, During continued vagal stimulation, an idioventricular escape focus emerges, having a regular rhythm. Right, On cessation of vagal stimulation (arrow), there is a postvagal sinus tachycardia.

FIGS. 7A-7D Hematoxylin and eosin stain of the site of hMSCs injection.

(A) H&E stain showing basophilic-stained stem cells and normal myocardium. (B) and (C) show, respectively, vimentin and CD44 staining of a node of hMSCs in canine myocardium. (D) Detail of vimentin-stained cells interspersed with myocardium. Magnification ×100 (A) and ×400 (B through D).

Figure 8:
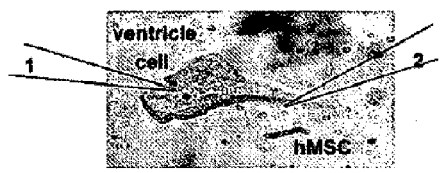
Figure 8:
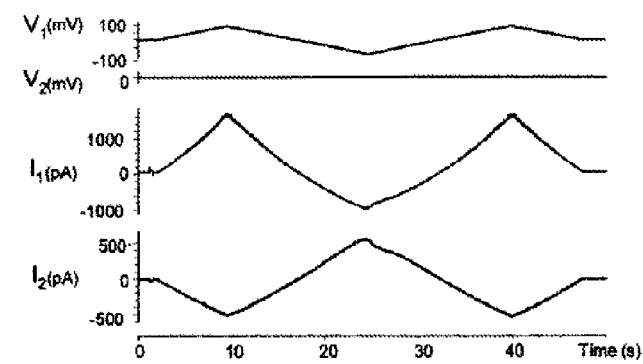
Figure 8:
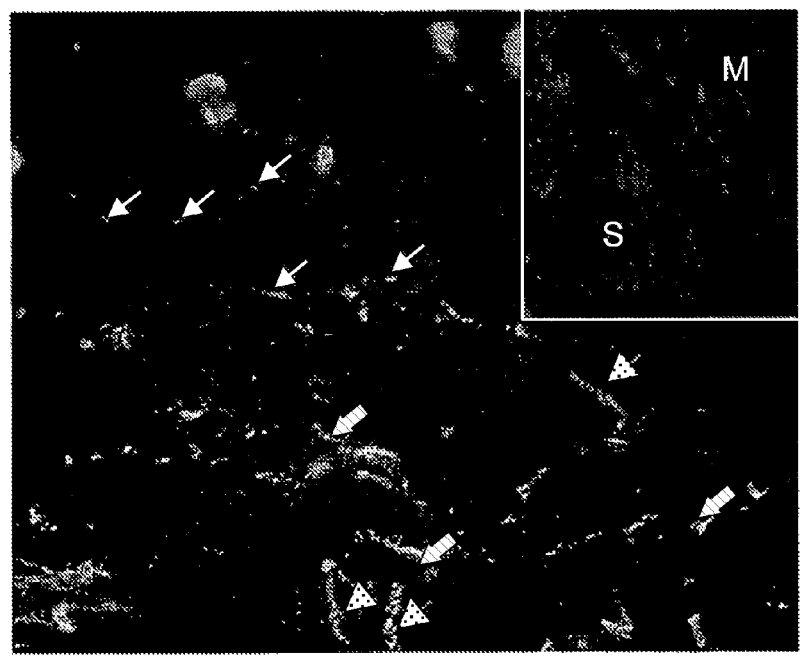

FIG. 8 Gap junctions between an hMSC-canine ventricular myocyte pair.

(A) Phase-contrast micrograph of a hMSC-myocyte pair and locations of pipettes 1 and 2. (B) Voltage ramp ($V_1 = \pm 100$ mV; $V_2 = 0$) applied to the canine myocyte evoked current flow through the patch pipettes attached in whole-cell mode to the myocyte, $I_1$, and hMSC, $I_2$. Currents recorded from the stepped myocyte, $I_1$, represent the sum of two components, a junctional current and a membrane current in the myocyte. The mirror current, $I_2$, recorded from the nonstepped hMSC corresponds to the junctional current, $I_j$, between the hMSC-myocyte pair. (C) Immunostaining for Cx43 in a region of interface between an injection site and myocardium. DAPI staining reveals nuclei. Arrows are purple, intercalated discs; white, Cx43 staining between hMSCs; red, Cx43 staining between hMSCs and myocytes. Inset, DAPI and EGFP antibody staining of a section from another animal, which was subjected to paraformaldehyde fixation and immunostained with anti-EGFP and DAPI to verify that injection sites contained hMSCs. M indicates myocardium; S, hMSC.

DETAILED DESCRIPTION OF THE INVENTION

Definitions

As used in this application, except as otherwise expressly provided herein, each of the following terms shall have the meaning set forth below.

As used herein, "administering" can be effected or performed using any of the various methods and delivery systems known to those skilled in the art. The administering can be performed, for example, intravenously, orally, nasally, via implant, transmucosally, transdermally, intramuscularly, and subcutaneously. The following delivery systems, which employ a number of routinely used pharmaceutically acceptable carriers, are only representative of the many embodiments envisioned for administering compositions according to the instant methods.

As used herein, "agent" shall include, without limitation, an organic compound, a nucleic acid, a polypeptide, a lipid, and a carbohydrate. Agents include, for example, agents which are known with respect to structure and/or function, and those which are not known with respect to structure or function. In a particular embodiment, an agent is known to have a given structure and effect in connection with a non-neurological disorder, such as depression, but is not known to have a given effect in connection with a neurological disorder.

As used herein, "cardiac myocytes" means myocytes derived from muscle or conductive tissue of a heart, either isolated or in culture, and capable of initiating a current.

As used herein, "gene construct" shall mean a genetically engineered cell.

As used herein, "HERG gene" means the human ether-a-go-go related gene which generates the $I_{Kr}$ current that is recorded from isolated cardiac myocytes.

As used herein, "subject" shall mean any animal, such as a non-human primate, mouse, rat, guinea pig, dog, cat, or rabbit.

As used herein, "syncytial cell" shall refer to a cell from a syncytial structure, such as the heart, bladder, liver, or gastrointestinal tract.

Embodiments of the Invention

This invention provides a method for determining the ability of a gene construct to alter the rhythm of a syncytial cell comprising: (i) contacting the gene construct to a syncytial cell; and (ii) determining whether the rhythm in the contacted syncytial cell is different than that in a syncytial cell to which the gene construct was not contacted, thereby determining whether the gene construct alters the rhythm of the syncytial cell.

In one embodiment of the instant method, the method comprises the steps of (a) contacting the gene construct to the syncytial cell, in vitro; (b) determining the rhythm of the contacted syncytial cell; and (c) comparing the rhythm so determined with the rhythm of the same syncytial cell prior to the contacting of the gene construct, the gene construct's ability to alter the rhythm of the syncytial cell being indicated when the rhythm of the contacted syncytial cell is different than the rhythm of the same syncytial cell prior to the contacting of the gene construct.

Step (b) can comprise, for example, the steps of: (i) administering a dye to the syncytial cell contacted to the gene construct; and (ii) monitoring the rhythm of the contacted syncytial cell with a photodiode. The dye used can be either a Ca-sensitive dye or a voltage sensitive dye. In another embodiment, step (b) comprises using edge detection. In a further embodiment, step (b) comprises using electrodes embedded in a testing well. In a still further embodiment, step (b) comprises using a glass patch electrode in a testing well.

The syncytial cell can be from a cardiac myocyte, a mammalian bladder, a mammalian liver, an arteriole, a mammalian gastrointestinal tract, a tumor originating from epithelial tissue or a tumor originating from smooth tissue.

This invention further provides a method for determining the ability of a gene construct to alter contractility of a syncytial cell comprising: (i) contacting the gene construct to the syncytial cell; and (ii) determining whether the contractility in the contacted syncytial cell is different than that in a syncytial cell to which the gene construct was not contacted, thereby determining whether the gene construct alters the contractility of the syncytial cell.

In one embodiment of the instant method, the method comprises the steps of (a) contacting the gene construct to the syncytial cell, in vitro; (b) determining the contractility of the contacted syncytial cell; and (c) comparing the contractility so determined with the contractility of the same syncytial cell prior to the contacting of the gene construct, the gene construct's ability to alter the contractility of the syncytial cell being indicated when the contractility of the contacted syncytial cell is different than the contractility of the same syncytial cell prior to the contacting of the gene construct.

This invention further provides a method of determining the coupling of a gene construct to a syncytial cell, comprising, (a) contacting the gene construct to the syncytial cell, in vitro; (b) determining the rhythm of the contacted syncytial cell; and (c) comparing the rhythm so determined with the rhythm of the same syncytial cell prior to the contacting of the gene construct, the coupling of the gene construct to the syncytial cell being indicated when the rhythm of the contacted syncytial cell is different than the rhythm of the same syncytial cell prior to the contacting of the gene construct was not contacted.

This invention further provides a method for producing a gene construct capable of altering the rhythm of a syncytial cell comprising the steps of (a) contacting a cell, known to have the ability to couple to a syncytial cell, with a gene to form a gene construct; (b) contacting the gene construct of step (a) to a syncytial cell, in vitro; (c) determining the rhythm of the contacted syncytial cell; and (d) comparing the rhythm so determined with the rhythm of the same syncytial cell prior to the contacting of the gene construct, the gene construct's ability to alter the rhythm of the syncytial cell being indicated when the rhythm of the contacted syncytial cell is different than the rhythm of the same syncytial cell prior to the contacting of the gene construct; and selecting the gene construct of step (d) which is determined to have the ability to alter the rhythm of the syncytial cell.

This invention further provides a method for producing a gene construct capable of altering the contractility of a syncytial cell comprising the steps of (a) contacting a cell, known to have the ability to couple to a syncytial cell, with a gene to form a gene construct; (b) contacting the gene construct of step (a) to a syncytial cell, in vitro; (c) determining the contractility of the contacted syncytial cell; (d) comparing the contractility so determined with the contractility of the same syncytial cell prior to contacting of the gene construct, the gene construct's ability to alter the contractility of the syncytial cell being indicated when the contractility of the contacted syncytial cell is different than the contractility of the same syncytial cell prior to the contacting of the gene construct; and (e) selecting the gene construct of step (d) which is determined to have the ability to alter the contractility of the syncytial cell.

Finally, this invention provides a method for producing a gene construct capable of coupling to a syncytial cell comprising the steps of (a) contacting a cell, known to have the ability to couple to a syncytial cell, with a gene to form a gene construct; (b) contacting the gene construct of step (a) to a syncytial cell, in vitro; (c) determining the rhythm of the contacted syncytial cell; (d) comparing the rhythm so determined with the rhythm of the same syncytial cell prior to the contacting of the gene construct, the coupling of the gene construct to the syncytial cell being indicated when the rhythm of the contacted syncytial cell is different than the rhythm of the same syncytial cell prior to the contacting of the gene construct; and (e) selecting the gene construct of step (d) which is determined to have coupled with the syncytial cell.

This invention is illustrated in the Experimental Details section which follows. This section is set forth to aid in an understanding of the invention but is not intended to, and should not be construed to limit in any way the invention as set forth in the claims which follow thereafter.

Experimental Details

Synopsis

The ability of human mesenchymal stem cells (hMSCs) to deliver a biological pacemaker to the heart was tested. hMSCs transfected with a cardiac pacemaker gene, mHCN2, by electroporation expressed high levels of $Cs^+$-sensitive current ($31.1\pm3.8$ pA/pF at $-150$ mV) activating in the diastolic potential range with reversal potential of $-37.5\pm1.0$ mV, confirming the expressed current as $I_f$-like. The expressed current responded to isoproterenol with an 11-mV positive shift in activation. Acetylcholine had no direct effect, but in the presence of isoproterenol, shifted activation 15 mV negative. Transfected hMSCs influenced beating rate in vitro when plated onto a localized region of a coverslip and overlaid with neonatal rat ventricular myocytes. The coculture beating rate was $93\pm16$ bpm when hMSCs were transfected with control plasmid (expressing only EGFP) and $161\pm4$ bpm when hMSCs were expressing both EGFP+mHCN2 ($P<0.05$). Next, $10^6$ hMSCs transfected with either control plasmid or mHCN2 gene construct were injected subepicardially in the canine left ventricular wall in situ. During sinus arrest, all control (EGFP) hearts had spontaneous rhythms ($45\pm1$ bpm, 2 of right-sided origin and 2 of left). In the EGFP+mHCN2 group, 5 of 6 animals developed spontaneous rhythms of left-sided origin (rate=$61\pm5$ bpm; $P<0.05$). Moreover, immunostaining of the injected regions demonstrated the presence of hMSCs forming gap junctions with adjacent myocytes. These findings demonstrate that genetically modified hMSCs can express functional HCN2 channels in vitro and in vivo, mimicking overexpression of HCN2 genes in cardiac myocytes, and represent a novel delivery system for pacemaker genes into the heart or other electrical syncytia.

hMSCs are effectively transfected by electroporation with a vector construct directing the expression of mouse HCN2 (mHCN2) as well as EGFP, and are capable of expressing functional mHCN2 channels in vitro. HCN2 expression in hMSCs provides an $I_f$-based current sufficient to change the beating rate of cocultured neonatal rat ventricular myocytes, and to drive the canine ventricle, mimicking the HCN2 overexpression by adenoviral constructs. (5) It was demonstrated that hMSCs make connexin proteins and form functional gap junctions that couple electrically with canine cardiac myocytes. Thus, an ex vivo gene therapy system using genetically modified hMSCs as a platform for delivery of pacemaker genes into the heart was developed.

Materials and Methods

Human Mesenchymal Stem Cell Maintenance and Transfection

Human mesenchymal stem cells (Poietics hMSC; mesenchymal stem cells, human bone marrow) were purchased from Clonetics/BioWhittaker (Walkersville, Md.) and cultured in MSC growing medium (Poietics MSCGM; BioWhittaker) at 37° C. in a humidified atmosphere of 5% $CO_2$. Cells were used from passages 2 to 4. A full-length mHCN2 cDNA was subcloned into a pIRES2-EGFP vector (BD Biosciences Clontech). Cells were transfected by electroporation using the Amaxa Biosystems Nucleofector (Amaxa) technology. (8) Expression of EGFP after 24 to 48 hours revealed transfection efficiency of 30% to 45%.

Patch-Clamp Studies of $I_{HCN2}$ Expressed in hMSCs

Whole-cell patch clamp were used to study membrane currents in control hMSCs and those transfected with mHCN2, the gene encoding the α-subunit of the pacemaker current, $I_f$. Expressed $I_f$ (ie, $I_{HCN2}$) was measured under voltage-clamp by an Axopatch-1B (Axon Instruments) amplifier. Patch electrode resistance was 4 to 6 MΩ before sealing. Cells were constantly superfused using a gravitational perfusion system with a complete change of the chamber solutions in about 0.5 minutes. The temperature of the bath as well as of the perfusion solution was kept constant at 35±0.5° C. The pipette solution was filled with (in mmol/L) KCl 50, K-aspartate 80, $MgCl_2$ 1, Mg-ATP 3, EGTA 10, and HEPES 10 (pH adjusted to 7.2 with KOH). The external solution contained (in mmol/L) NaCl 137.7, KCl 5.4, NaOH 2.3, $CaCl_2$ 1.8, $MgCl_2$ 1, Glucose 10, HEPES 5, and $BaCl_2$ 2 (pH adjusted to 7.4 with NaOH). The membrane capacity was measured by applying a voltage clamp step and current densities are expressed as the value of peak current per capacity.

Dual Patch-Clamp Studies of Gap Junctions

Canine cardiac ventricular myocytes were isolated as previously described. (9) Primary cultures of the myocytes were maintained using procedures described for mouse myocytes. (10) They were plated at 0.5 to $1\times10^4$ cells/cm$^2$ in MEM containing 2.5% fetal bovine serum (FBS) and 1% PS onto mouse laminin (10 µg/mL) precoated coverslips. After 1 hour of culture in a 5% $CO_2$ incubator at 37° C., the medium was changed to FBS-free MEM. hMSCs were added and coculture was maintained in DMEM with 5% FBS. Cell Tracker green (Molecular Probes) was used to distinguish hMSCs from HeLa cells in coculture in all experiments. (11) Glass coverslips with adherent cells were transferred to an experimental chamber perfused at room temperature (≈22° C.) with bath solution containing (in mmol/L) NaCl 150, KCl 10, $CaCl_2$ 2, HEPES 5 (pH 7.4), and glucose 5. The patch pipettes were filled with solution containing (in mmol/L) K$^+$ aspartate[31] 120, NaCl 10, MgATP 3, HEPES 5 (pH 7.2), and EGTA 10 (pCa≈8), filtered through 0.22-µm pores. When filled, the resistance of the pipettes measured 1 to 2 MΩ. Experiments were performed on cell pairs using a double voltage-clamp. This method permitted control of the membrane potential ($V_m$) and measurements of the associated junctional currents ($I_j$).

Action Potential Recordings in Coculture hMSCs were plated onto fibronectin-coated 9×22-mm coverslips, using a cloning cylinder to restrict the initial plating to an approximate 4-mm diameter circular area. The cells expressed either EGFP alone or EGFP+mHCN2. Four hours later, the cloning cylinder was removed and neonatal rat ventricular myocytes, prepared as described previously, (12) were plated over the entire coverslip. Four to five days later, the coverslips were placed in a superfusion chamber maintained at 35° C. and action potentials recorded from near the center of the coverslip using a perforated patch electrode (12) and normal physiological solution containing (in mmol/L) NaCl 140, NaOH 2.3, $MgCl_2$ 1, KCl 5.4, $CaCl_2$ 1.0, HEPES 5, and glucose 10; pH 7.4. Pipette solution included (in mmol/L) aspartic acid 130, KOH 146, NaCl 10, $CaCl_2$ 2, EGTA-KOH 5, Mg-ATP 2, and HEPES-KOH 10; pH 7.2. Recordings were conducted with an Axopatch 200 amplifier and PClamp 8 software (Axon Instruments). The perforated patch technique was used, and amphotericin B (400 µg/mL, Sigma) was added to the pipette solution.

In Vivo Studies in Canine Ventricle

Stem cells were prepared as above. Under sterile conditions, after sodium thiopental induction (17 mg/kg IV) and inhalational isoflurane (1.5 to 2.5%) anesthesia, 23- to 27-kg mongrel dogs (Team Associates, Dayville, Conn.) were subjected to a pericardiectomy. $10^6$ hMSCs containing HCN2+ GFP or GFP alone were then injected subepicardially in 0.6 mL of solution into the left ventricular anterior wall, approximately 2 mm deep to the epicardium via a 21-gauge needle. Animals recovered for 4 to 10 days, during which their cardiac rhythms were monitored. They then were anesthetized with isoflurane, as above. Both cervical vagal trunks were isolated, the chest opened, and ECGs monitored. Graded right and left vagal stimulation was performed via standard techniques (13) to suppress sinus rhythm such that escape pacemaker function might occur. Tissues were then removed for histological study.

Histological Methods

Unless otherwise indicated, samples of heart tissue were fixed in 10% buffered formalin, embedded in paraffin and sectioned at 4 or 6 micrometers. Some formalin-fixed sections were stained in a routine fashion with hematoxylin and eosin (H&E). Monoclonal mouse antibodies (DakoCytomation) raised against the vimentin and human CD 44 were used applying an avidin-biotin-peroxidase method. (14) Tissues stained immunohistochemically were then counterstained with hematoxylin. Positive and negative controls for immunohistochemical staining were used. hMSCs were distinguished from fibroblasts by CD 44 staining. The vimentin antibody intensely stains hMCSs but also stains most mesenchymal tissue. Other sections were treated to remove wax and rehydrated by exposure to xylene for 6 minutes with three rinses followed by similar exposures to 100%, 95%, 50% ethanol, deionized water, and PBS. The sections were then exposed to 30% hydrogen peroxide for 10 minutes and were again rinsed in PBS for 50 minutes. The rehydrated sections were exposed to a 0.01 mol/L citrate buffer, which was heated to a boil for 10 minutes and then allowed to cool to room temperature. Polyclonal antibodies raised against connexin 43 (Cx43; Zymed Laboratories Inc) were used.

Statistics

Results are presented as mean±SEM. Statistical significance was determined by Student's t test for unpaired data. A value of P<0.05 was considered significant.

Results

Transfection of hMSCs With mHCN2 and Demonstration of Pacemaker Current

Nontransfected hMSCs demonstrated no significant time-dependent currents during hyperpolarizations (FIG. 1A). MHCN2-transfected hMSCs expressed a large time-dependent inward current activating on hyperpolarizations up to −160 mV and deactivating during the following step to 20 mV (FIG. 1B). FIG. 1C shows the $I_f$ activation curve constructed from tail currents recorded in mHCN2-transfected hMSCs (see inset for sample currents). The data was fit with a Boltzmann two-state model, which yielded a midpoint ($V_{50}$) of −91.8±0.9 mV and a slope factor of 8.8±0.5 mV (n=9), similar to values for mHCN2 expression in oocytes and HEK 293 cells. (15, 16) These values are an approximation because the $I_f$ current density was large and its slow rundown was apparent, as in all other preparations. The results suggest $I_f$ should be activated at diastolic potentials in the hMSCs if they are well coupled by gap junctions to ventricular myocytes. The experiments illustrated in FIG. 2 were executed to confirm the expressed current was $I_f$. The voltage protocol (see FIG. 2 legend for description) allowed us to determine the reversal potential of −37.5±1.0 mV (n=8). Given the extracellular [$K^+$] of 5.4 mmol/L, this reversal potential is consistent with the mixed selectivity of the $I_f$ channel to [$Na^+$] and [$K^+$]. (17) The effect of $Cs^+$ to block the expressed current were tested. $Cs^+$ (4 mmol/L) reversibly blocked the inward currents but had little effect on the outward deactivating tail currents, consistent with $Cs^+$ blockade of $I_f$. (18) In FIG. 2D, the fully activated I-V relationships for the $I_f$-like current were constructed. The plot reinforces the two major observations from the raw data. First, inward but not outward $I_f$-like currents are blocked by $Cs^+$, and second, the zero current indicates a mixed selectivity consistent with the known properties of $I_f$. In a separate protocol $I_f$ density at −150 mV was 31.1±3.8 pA/pF (n=17). Membrane capacity for the transfected hMSCs was 110.8±9.0 pF (n=17).

Neurohumoral Regulation of $I_{HCN2}$

Figure 3:
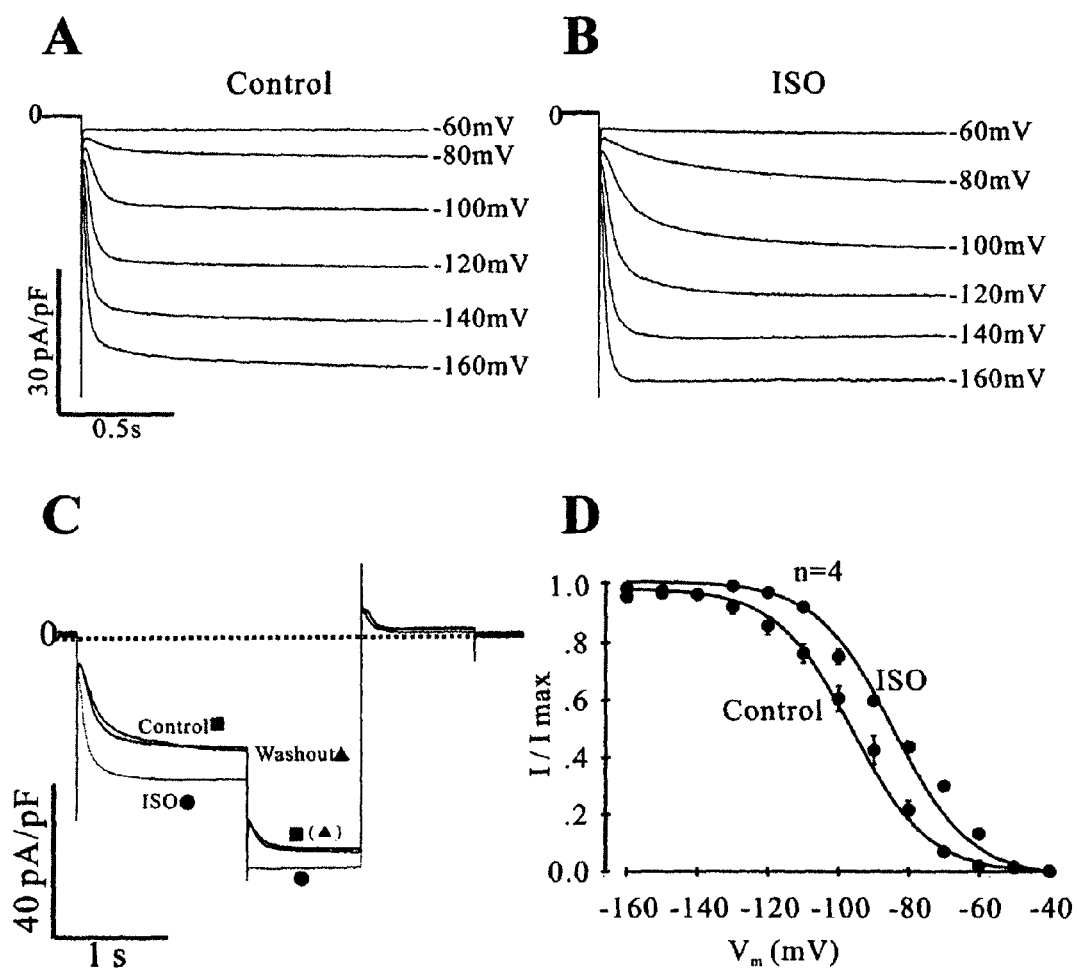
Figure 4:
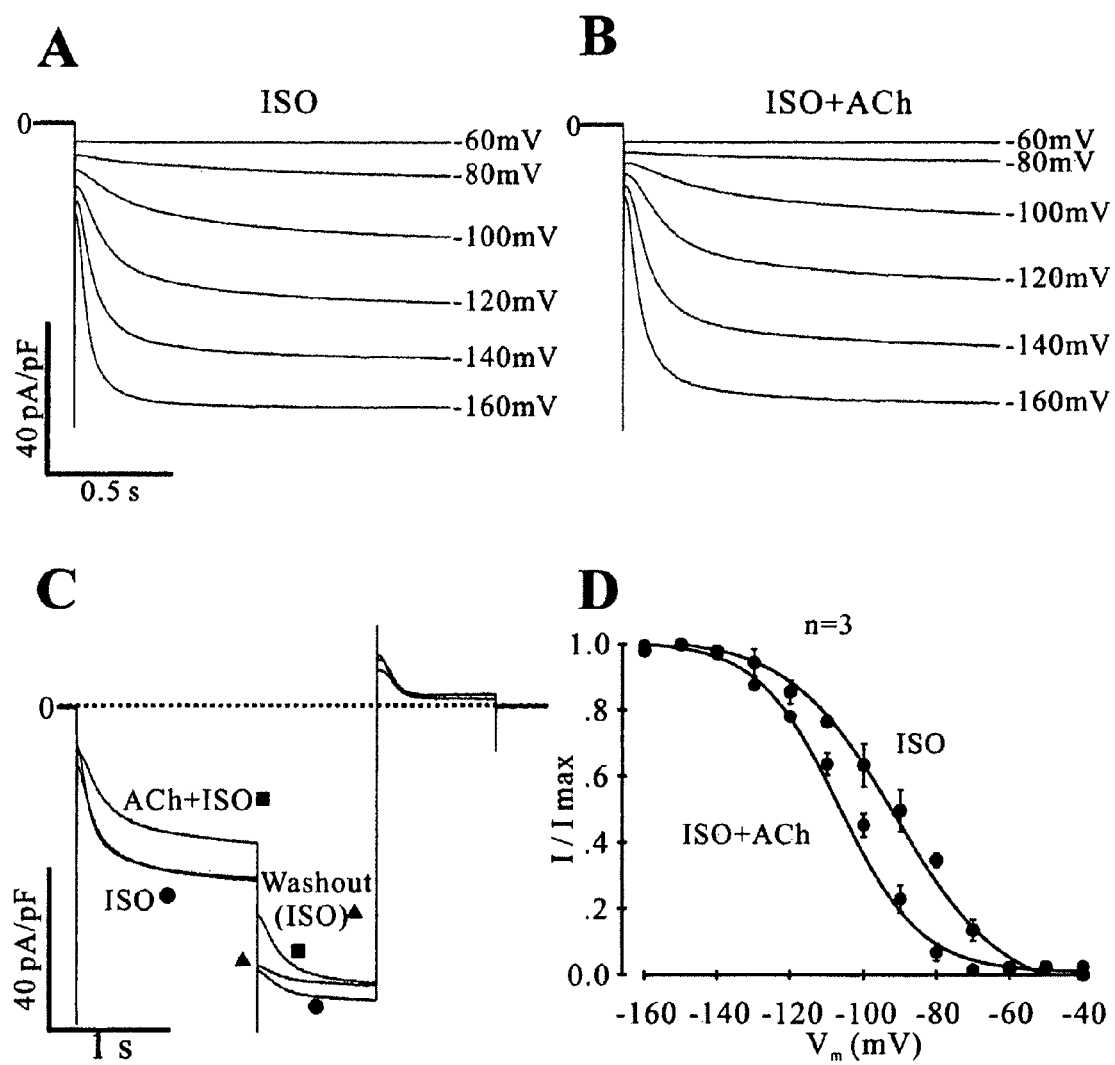

A potential advantage of biological over electronic pacemakers is their hormonal regulation. The effects of β-adrenergic and muscarinic agonists on $I_f$ recorded in the hMSCs were examined (FIGS. 3 and 4). FIGS. 3A and 3B demonstrate that the currents at −80 and −100 mV in isoproterenol are larger than those in control, whereas the currents in both conditions are almost equal at −160 mV. This voltage-dependent difference is expected for a shift in the activation curve (FIG. 3D). The half activation voltage ($V_{50}$) was −96±0.9 mV in control and −84.4±0.2 mV in isoproterenol (n=4, P<0.01). The slope factor was 10.9±0.5 mV in control and 11.0±0.2 mV in isoproterenol (P>0.05). Using a two-pulse protocol to illustrate the shift in activation, the time-dependent current in the presence of isoproterenol is larger in response to the first step than control and smaller in response to the second step (FIG. 3C). This is consistent with an ISO-induced positive shift in $I_f$ activation. Acetylcholine had no direct effect on the time-dependent current (n=3), due either to the absence of muscarinic receptors or to a low basal level of cAMP that could not be further reduced by acetylcholine inhibition of adenylyl cyclase. Therefore, it was further tested whether acetylcholine could reverse the actions of isoproterenol (FIG. 4). Examination of the response to the step hyperpolarizations to −80 and −100 mV indicate that addition of acetylcholine reduces the membrane currents. However, they are almost identical at −160 mV (FIGS. 4A and 4B), consistent with a negative shift in activation induced by acetylcholine. FIG. 4D shows the activation curves in isoproterenol and isoproterenol+acetylcholine. The $V_{50}$s were −91.3±1.1 mV for isoproterenol and −106.6±0.8 mV for isoproterenol+acetylcholine (n=3, P<0.05). The slope factors were 14.6±0.9 mV in isoproterenol and 11.1±0.9 mV (n=3, P<0.05). A two-pulse protocol was also used (FIG. 4C). The response to the first voltage step is larger in isoproterenol than in isoproterenol+acetylcholine, whereas the reverse is true for the second step. This is again consistent with a negative shift in activation induced by addition of acetylcholine. These results demonstrate that the hMSCs transfected with mHCN2 should respond to β-adrenergic and muscarinic agonists.

mHCN2-Transfected hMSCs Modulation of Impulse Initiation by Cardiac Myocytes

Figure 5:
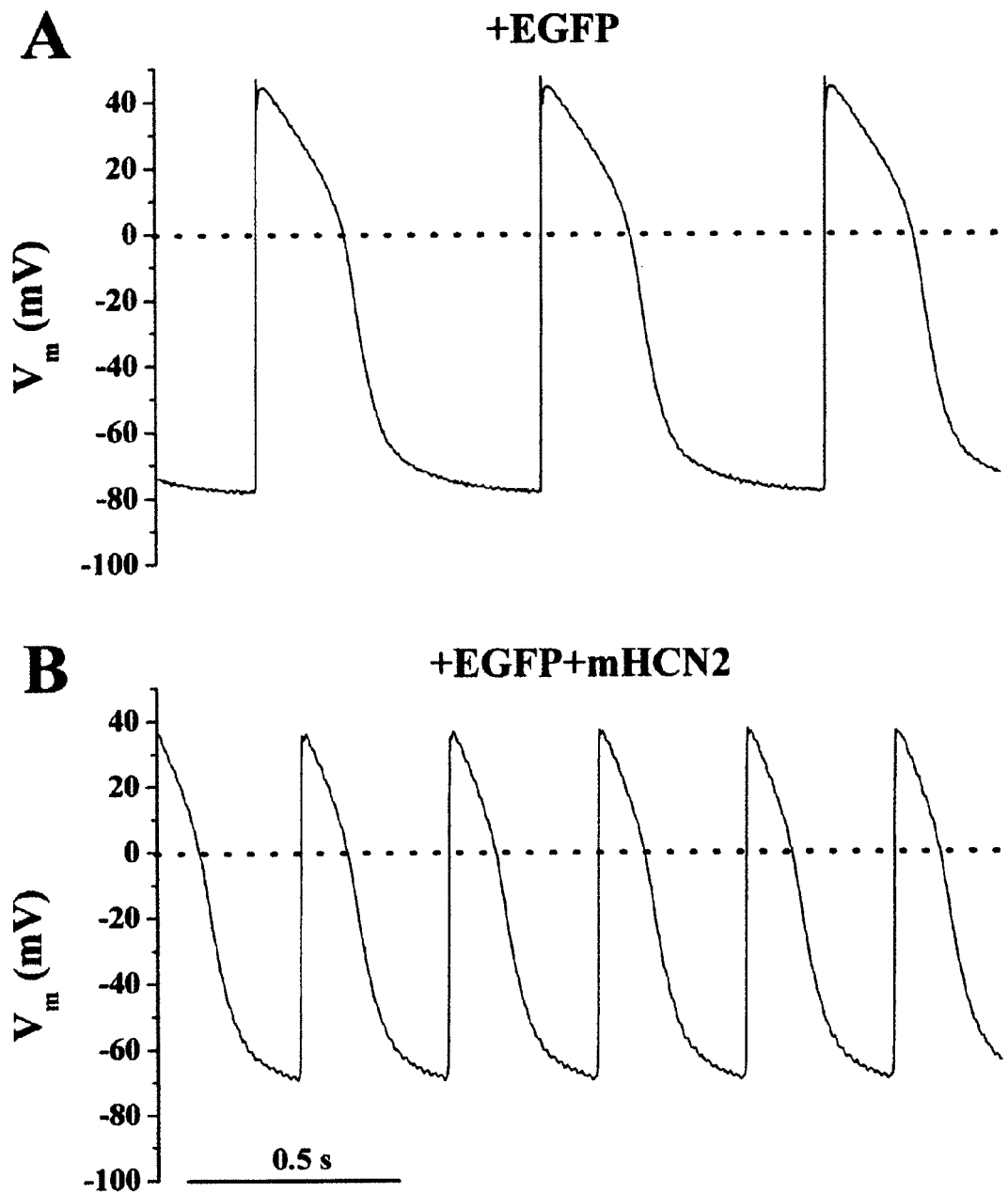

Having expressed the pacemaker gene in hMSCs, it was hypothesized that the mHCN2-transfected hMSCs could influence excitability of coupled heart cells. Maximum diastolic potential was −74±1 mV (n=5) in neonatal rat ventricular myocytes cocultured with EGFP expressing hMSCs and −67±2 mV (n=6) in myocytes cocultured with hMSCs expressing mHCN2 (P<0.05). Spontaneous rate was 93±16 bpm in the former group (n=5) and 161±4 bpm in the latter (n=6, P<0.05). The reduced maximum diastolic potential is consistent with the observed threshold potential of the expressed current in the mHCN2-transfected hMSCs, and indicates the influence of this depolarizing current on the electrically coupled myocytes. Representative action potentials are shown in FIG. 5.

The monitoring chamber is a PC-based data acquisition system (Multi Channel Systems, Reutlingen, Germany), consisting of multi-electrode arrays (MEAs), pre- and filter-amplifiers, a data acquisition board and software. The MEA consists of a 50×50 mm glass substrate, in the center of which is embedded a 1.4×1.44 m matrix of 60 titanium-nitride, gold contact, 30 μm diameter electrodes insulated with silicone nitride, with an interelectrode distance of 200 μm respectively (note that there are no electrodes at the corner of the matrix). Cultures are stimulated using one of the four pairs of stimulating electrodes (250 μm×50 μm) located 2 mm from each of the four external rows of recording electrodes. Data is recorded at 10 kHz with 12-bit precision. To permit data recording, the MEA is removed from the incubator, constantly perfused with fresh culture medium, and saturated with a gas mixture consisting of 5% $CO_2$ and 95% air at 37° C.

mHCN2-Transfected hMSCs as a Biological Pacemaker in Intact Canine Heart

Given the demonstration of functional coupling of mHCN2-expressing hMSCs to myocytes in vitro, they were then injected into canine heart in situ (see Materials and Methods) to test whether pacemaker function was demonstrable. During sinus arrest, escape pacemaker function can originate in the left or right ventricle, as occurred here, with two of four animals receiving hMSCs expressing EGFP alone developing left and two developing right ventricular escape rhythms. In contrast, five of six animals receiving hMSCs expressing EGFP+mHCN2 developed rhythms originating from and pace-mapped to the left ventricle at a site whose origin approximated that of the hMSC injection. Moreover, the idioventricular rates of these animals was 61±5 versus 45±1 bpm in animals receiving hMSCs expressing EGFP alone (P<0.05). A representative experiment is shown in FIG. 6.

Figure 7:
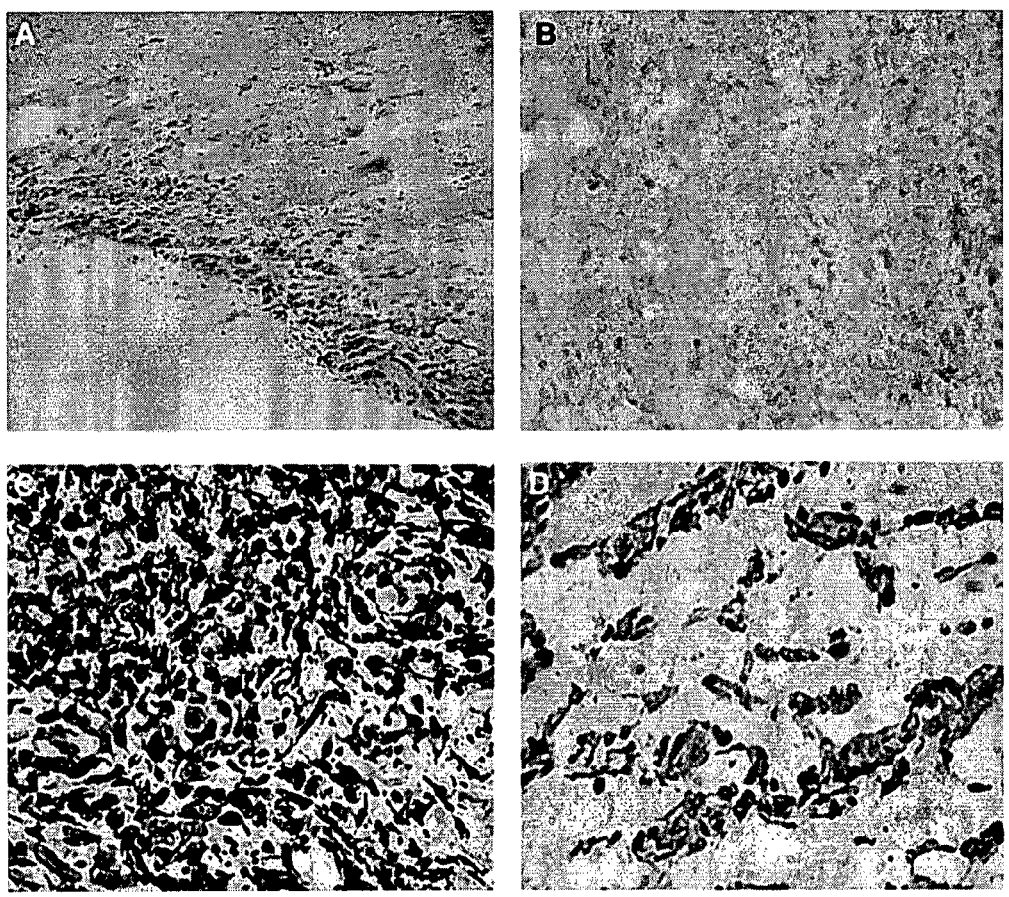

Hematoxylin and eosin stain of the site of hMSCs injection revealed normal cardiac myocytes and dense areas of basophilic infiltration adjacent to the needle track (FIG. 7A). The hMSCs were easily identified by their size (10 to 20 μm in diameter), large hyperchromatic nuclei, and scanty, deeply basophilic cytoplasm with no matrix. Although the hMSCs had a characteristic appearance with H&E staining, they were more precisely identified by using immunohistochemical stains. The hMSCs stained intensely for vimentin (eg, FIG. 7B), a marker of cells of mesenchymal origin. The same regions also were positive for human CD44 (eg, FIG. 7C). Interdigitation between hMSCs and myocardium was very clear (eg, FIG. 7D).

hMSCs Form Gap Junctions with Cardiac Myocytes in Vitro and In Vivo

To test whether the hMSCs couple electrically with cardiac myocytes, hMSCs were cocultured with adult canine ventricular myocytes. Myocytes were dissociated and plated for between 12 and 72 hours before coculture with hMSCs. Measurement of coupling occurred 6 to 12 hours after adding hMSCs to the myocyte culture. Preliminary observations reveal that stem cells couple to cardiac cells. FIG. 8A illustrates one example of an hMSC-myocyte pair in coculture; it is one of four so far observed. For heterologous pairs identification the hMSCs were tagged with Cell Tracker green (Molecular Probes). (11) A bipolar voltage-ramp protocol was used to alter transjunctional voltage $V_j$ ($V_2$-$V_1$) over ±100 mV range at 200 mV/15-second rate (see $V_1$ and $V_2$) and is shown in FIG. 8B. The ramp pulse was applied to the myocyte ($V_1$) while membrane potential of the hMSC was kept at 0 mV ($V_2$). The associated sister currents, $I_1$ and $I_2$, were recorded from the myocyte and hMSC, respectively. The currents followed the voltage-ramp profile demonstrating gap junction coupling of the heterologous hMSC-myocyte pair. The current, $I_2$, obtained from the nonstepped hMSC, reflects a coupling current, $I_j$. This record demonstrates effective coupling of the hMSC to the ventricular myocyte. FIG. 8C shows immunohistochemical staining with anti-Cx43 antibodies of the site of the injection of hMSCs into the canine heart. Intercalated discs are revealed in the myocardium (see purple arrow), whereas small punctate staining for Cx43 is seen between hMSCs (white arrows). There is also Cx43 staining at interfaces between hMSCs and myocytes (red arrows). The inset of FIG. 8C shows a section from a piece of myocardium (fixed in 4% paraformaldehyde in 0.1 mol/L phosphate buffer at pH of 7.4 at 4° C. and subsequently treated as described by Walcott et al (15)) injected with hMSCs expressing EGFP plus HCN2. The red staining from the secondary antibody to EGFP illustrates localization of hMSCs, whereas the blue staining illustrates cell nuclei. A significant majority of the clustered cells are hMSCs.

Discussion

Pacemaker implantation is a primary treatment for complete heart block or sinus node dysfunction. The current therapy uses electronic devices with high reliability and low morbidity. Nevertheless, such devices are not optimal because they lack the biological responsiveness of native tissues. Recently several approaches have been attempted to provide biological pacemaker function. Included among these attempts have been an upregulation of $\beta_2$-adrenergic receptors, a downregulation of the background K$^+$ current $I_{K1}$ and our own previous studies with overexpression of the HCN2 gene, the molecular correlate of the endogenous cardiac pacemaker current $I_f$. (2-6) In these latter studies, it was shown that HCN2 overexpression locally in left atrium or in the proximal bundle-branch system induces both $I_f$-like currents and in situ pacemaker function in the recipient myocytes. The unique voltage dependence of the $I_f$ conductance results in current flow during diastole but not during the action potential plateau, limiting possible complications attendant to significant alterations of the action potential waveform. Although an adenoviral construct has been used to deliver the HCN2 gene to the heart, (5, 6) this approach is not optimal because adenoviruses are episomal and the nucleic acids they deliver do not integrate into genome. Other viral systems are accompanied by a number of serious drawbacks that hinder their use in vivo.

An alternative means for fabricating biological pacemakers is via embryonic stem cells, which can be differentiated along a cardiac lineage and might provide a platform for cell-based control of cardiac rhythm. Embryonic stem cells can make functional gap junctions and generate spontaneous electrical activity. (20) However because of their immunogenicity, rejection is a serious consideration. Moreover, as with hMSCs, embryonic stem cell preparations are not spatially uniform and the proper engineering of both cell-based systems presents a challenge in designing in vivo biological pacemakers.

For several reasons, hMSCs are an attractive cellular vehicle for gene delivery applications. They can be obtained in relatively large numbers through a standard clinical procedure. hMSCs are easily expanded in culture and capable of long-term transgene expression. (21) Their administration can be autologous or via banked stores, given evidence that they may be immunopriviliged. (22) Long-term function of such a pacemaker is based on prolonged expression of mHCN2, which in turn requires integration into the genome of hMSCs. Random integration increases the possibility of disruption of genes involved in the cell cycle or tumor suppression, or may cause epigenetic changes. However, the ex vivo transfection method used here allows the DNA integration site to be evaluated before use and the cell carriers can be engineered with fail-safe death mechanisms.

The objective of this study was to test the feasibility of using genetically modified hMSCs as a platform for systemic delivery of pacemaker genes into the heart. HCN2 served as the model system for this study. The genetically engineered hMSCs expressed an $I_f$-like current and were capable of increasing the spontaneous beating rate of cocultured rat neonatal myocytes and originating a ventricular rhythm during vagally induced sinus arrest in the canine heart. Control hMSCs expressing only EGFP did not exert these effects either in vitro or in vivo. Thus, the electrical effects of the hMSCs transfected with the mHCN2 gene were similar to the effects of overexpression of the same gene in the myocytes in in vitro and in vivo systems. These findings suggest that hMSCs may serve as an alternative approach for the delivery of pacemaker genes for cardiac implantation.

In sinus node myocytes the HCN gene generates an inward current necessary for cardiac excitation. Unlike sinoatrial node cells, mHCN2-transfected hMSCs are not excitable, because they lack the other currents required to generate an action potential. However, these cells are able to generate a depolarizing current, which spreads to coupled myocytes, driving myocytes to threshold. It is hypothesized that as long as the hMSCs contain the pacemaker gene and couple to cardiac myocytes via gap junctions, they will function as a cardiac pacemaker in an analogous manner to the normal primary pacemaker the sinoatrial node. It was demonstrated using dual patch technique that hMSCs form gap junctions that couple electrically with canine cardiac myocytes. The coupling between engrafted hMSCs and cardiac myocytes was also shown by immunohistochemical staining of the tissues isolated from the site of hMSC injection using anti-connexin 43 antibodies. Within an injection site, the clusters of cells were vimentin and CD44 positive, and it also demonstrated that a significant majority of the cluster of cells were EGFP positive, thereby confirming their identity as hMSCs. A recent report has suggested that mouse MSCs can fuse with mouse myocytes in vivo with a fusion rate of 0.005%. (23) This possibility has not been ruled out, but at the fusion rate reported by Morimoto et al, (23) only 50 hMSCs of the million cells injected would fuse.

There are limitations to the approach used in this study. First, the hMSCs were delivered to the free wall myocardium, not an optimal site for ordered contraction. However, catheter approaches have been recently used to insert pacemaker genes into the canine left bundle branch system. (6) Such a locus offers the possibility of more ordered and normal activation and contraction than is the case with a pacemaker residing in the free wall. Before this approach is used for hMSCs, catheter modification may need to occur to optimize injection of cells of the size of an hMSC without cell injury or destruction.

Another question relates to the duration of efficacy of these pacemakers. The present study was concerned with demonstrating the feasibility of using hMSCs as a gene delivery system. Because the studies in vivo lasted only 3 to 10 days, transient transfections were sufficient. Before this approach can be considered clinically relevant, far longer periods of study will be required. In this regard, the transfected cells maintain their green fluorescence for at least 3 months when grown on antibiotic to select stably expressing cells. This indicates selection for stable clones expressing mHCN2, so it is likely that persistence of expression will not pose significant difficulties for more prolonged studies. However, it remains to be determined if the differentiation state of the hMSCs is altered in situ in the long term, or whether such differentiation would affect mHCN2 expression or biophysical properties. In addition, a murine gene, which is quite close but not completely identical in sequence to the human gene was used here. Not only would it be most advantageous to use human genes, but the exploration of various mutations to optimize activation and recovery characteristics, as well as neurohumoral response would be desirable. Such approaches are currently being explored.

The delivery of hMSCs expressing mHCN2 to the canine heart is not only a demonstration of feasibility of preparing hMSC-based biological pacemakers, but is the first concrete example of a general principle: hMSCs can be used to deliver a variety of genes to influence the function of syncytial tissues. One alternative potential cardiovascular application is delivery of $K^+$ channel genes to hyperpolarize vascular smooth muscle inducing relaxation. Indeed, the payload delivered by hMSCs need not be restricted to membrane channels: any gene product or small molecule that can permeate gap junctions (MW <1000, minor diameter <1.2. nm) can be incorporated into the hMSCs and delivered to a syncytial tissue as its therapeutic target.

REFERENCES

1. Zivin A, Bardy G H. Cardiac pacemakers. In: Spooner P M, Rosen M R, eds. Foundations of Cardiac Arrhythmias. New York, N.Y.: Marcel Dekker, Inc: 2001; 571-598.
2. Edelberg J M, Aird W C, Rosenberg R D. Enhancement of murine cardiac chronotropy by the molecular transfer of the human $\beta_2$-adrenergic receptor cDNA. J Clin Invest. 1998; 101: 337-343.
3. Edelberg J M, Huang D T, Josephson M E, Rosenberg R D. Molecular enhancement of porcine cardiac chronotropy. Heart. 2001; 86: 559-562.
4. Miake J, Marban E, Nuss H B. Gene therapy: biological pacemaker created by gene transfer. Nature. 2002; 419: 132-133.
5. Qu J, Plotnikov A N, Danilo P Jr, Slapakova I, Cohen I S, Robinson R B, Rosen M R. Expression and function of a biological pacemaker in canine heart. Circulation. 2003; 107: 1106-1109.
6. Plotnikov A N, Sosunov E A, Qu J, Shlapakova I, Anyukhovsky E P, Liu L, Janse M J, Brink P R, Cohen I S, Robinson R B, Danilo P Jr, Rosen M R. A biological pacemaker implanted in the canine left bundle branch provides ventricular escape rhythms having physiologically acceptable rates. Circulation. 2004; 109: 506-512.
7. Gepstein L. Derivation and potential applications of human embryonic stem cells. Circ Res. 2002; 91: 866-876.
8. Hamm A, Krott N, Breibach I, Blindt R, Bosserhoff A K. Efficient transfection method for primary cells. Tissue Eng. 2002; 8: 235-245.
9. Yu H, Gao J, Wang H, Wymore R, Steinberg S, McKinnon D, Rosen M R, Cohen I S. Effects of the renin-angiotensin system on the current $I_{to}$ in epicardial and endocardial ventricular myocytes from the canine heart. Circ Res. 2000; 86: 1062-1068.
10. Zhou Y Y, Wang S Q, Zhu W Z, Chruscinski A, Kobilka B K, Ziman B, Wang S, Lakatta E G, Cheng H, Xiao R P. Culture and adenoviral infection of adult mouse cardiac myocytes: methods for cellular genetic physiology. Am J Physiol (Heart Circ Physiol). 2000; 279: H429-H436.
11. Valiunas V, Weingart R, Brink P R. Formation of heterotypic gap junction channels by connexins 40 and 43. Circ Res. 2000; 86: e42-e49.
12. Protas L, Robinson R B. Neuropeptide Y contributes to innervation-dependent increase in $I_{Ca,L}$ via ventricular Y2 receptors. Am J Physiol. 1999; 277: H940-H946.
13. Rosenshtraukh L, Danilo P Jr, Anyukhovsky E P, Steinberg S F, Rybin V, Brittain-Valenti K, Molina-Viamonte V, Rosen M R. Mechanisms for vagal modulation of ventricular repolarization and of coronary occlusion-induced lethal arrhythmias in cats. Circ Res. 1994; 75: 722-732.
14. Hsu S, Raine L. Protein A, avidin, and biotin in immunohistochemistry. J Histochem Cytochem. 1981; 29: 1349-1353.
15. Yu H, Wu J, Potapova I, Wymore R T, Holmes B, Zuckerman J, Pan Z, Wang H, Shi W, Robinson R B, El-Maghrabi M R, Benjamin W, Dixon J, McKinnon D, Cohen I S, Wymore R. MinK-related peptide 1: A β subunit for the HCN ion channel subunit family enhances expression and speeds activation. Circ Res. 2001; 88: e84-e87.
16. Moosmang S, Stieber J, Zong X, Biel M, Hofmann F, Ludwig A. Cellular expression and functional characterization of four hyperpolarization-activated pacemaker channels in cardiac and neuronal tissues. Eur J Biochem. 2001; 268: 1646-1652.

17. DiFrancesco D. A study of the ionic nature of the pacemaker current in calf Purkinje fibres. *J Physiol.* 1981; 314: 377-393.
18. DiFrancesco D. Block and activation of the pacemaker channel in calf Purkinje fibres: effects of potassium, caesium and rubidium. *J Physiol.* 1982; 329: 485-507.
19. Walcott B, Moore L C, Birzgalis A, Claros N, Valiunas V, Ott T, Willecke C, Brink P R. The role of gap junctions in fluid secretion of lacrimal glands. *Am J Physiol.* 2002; 282: C501-C507.
20. Boheler K R, Czy J, Tweedie D, Yang H T, Anisimov S V, Wobus A M. Differentiation of pluripotent embryonic stem cells into cardiomyocytes. *Circ Res.* 2002; 91: 189-201.
21. Zhang X Y, La Russa V F, Bao L, Kolls J, Schwarzenberger P, Reiser J. Lentiviral vectors for sustained transgene expression in human bone marrow-derived stromal cells. *Mol Ther.* 2002; 5: 555-565.
22. Liechty K W, MacKenzie T C, Shaaban A F, Radu A, Moseley A M, Deans R, Marshak D R, Flake A W. Human mesenchymal stem cells engraft and demonstrate site-specific differentiation after in utero transplantation in sheep. *Nat Med.* 2000; 6: 1282-1286.
23. Morimoto Y, Davis B H, van der Bos E-J, McMichael M D, Taylor D. Transplanted bone marrow derived mesenchymal stem cells fuse with cardiomyocytes. *Circulation.* 2003; 108: IV-548. Abstract.

What is claimed is:

1. A method comprising:
   (i) providing a first and a second genetically modified cell that are either both cardiomyocytes or both mesenchymal stem cells (MSCs) comprising a nucleic acid construct, wherein the construct in the first cell comprises a gene that is expressed by the first cell, and the construct in the second cell does not comprise the gene;
   (ii) providing a first and a second cardiac syncytial cell;
   (iii) determining a baseline rhythm for the first and second cardiac syncytial cells in vitro;
   (iv) contacting the first cardiac syncytial cell with the first cell of step (i) and contacting the second cardiac syncytial cell with the second cell of step (i) in vitro;
   (v) determining the rhythm of the first and second cardiac syncytial cells after the contacting step (iv) in vitro; and
   (vi) identifying the first cell of step (i) as a cell that alters rhythm of a cardiac syncytial cell if the rhythm of the first cardiac syncytial cell determined in step (v) differs from its baseline rhythm determined in step (iii), and the rhythm of the second cardiac syncytial cell determined in step (v) does not differ from its baseline rhythm determined in step (iii).

2. The method of claim 1, wherein the gene is a gene encoding a hyperpolarization-activated, cyclic nucleotide-gated 2 (HCN2) channel.

3. The method of claim 1, wherein rhythm is determined by photodiode detection of dye administered to the first and second cardiac syncytial cells.

4. The method of claim 3, wherein the dye is a Ca-sensitive dye.

5. The method of claim 4, wherein the Ca-sensitive dye is fluo-3.

6. The method of claim 3, wherein the dye is a voltage sensitive dye.

7. The method of claim 1, wherein rhythm is determined by edge detection in said first and second cardiac syncytial cells.

8. The method of claim 1, wherein rhythm is determined with electrodes embedded in a test well.

9. The method of claim 8, wherein the electrodes comprise one 150×30 micrometer diameter stimulating electrode and one 30 micrometer electrode.

10. The method of claim 9, wherein the testing well has an inner diameter of at least 3 mm by 3 mm.

11. The method of claim 1, wherein rhythm is determined with a glass patch electrode in a testing well.

12. The method of claim 11, wherein the testing well has an inner diameter of at least 3 mm by 3 mm.

13. A method comprising:
   (i) providing a first and a second genetically modified cell that are either both cardiomyocytes or both mesenchymal stem cells (MSCs) comprising a nucleic acid construct, wherein the construct in the first cell comprises a gene that is expressed by the first cell, and the construct in the second cell does not comprise the gene
   (ii) providing a first and second cardiac syncytial cell;
   (iii) determining a baseline contractility for the first and second cardiac syncytial cells in vitro;
   (iv) contacting the first cardiac syncytial cell with the first cell of step (i) and contacting the second cardiac syncytial cell with the second cell of step (i) in vitro;
   (v) determining the contractility of the first and second cardiac syncytial cells after the containing step (iv) in vitro; and
   (vi) identifying the first cell of step (i) as a cell that alters the contractility of a cardiac syncytial cell if the contractility of the first cardiac syncytial cell determined in step (v) differs from its baseline contractility determined in step (iii), and the contractility of the second cardiac syncytial cell determined in step (v) does not differ from its baseline contractility determined in step (iii).

14. The method of claim 13, wherein the gene is a gene encoding a hyperpolarization-activated, cyclic nucleotide-gated 2 (HCN2) channel.

15. A method comprising:
   (i) providing in vitro a cardiac syncytial cell and a genetically modified cell that is either a cardiomyocyte or a mesenchymal stem cell (MSC) comprising a nucleic acid construct comprising a gene that is expressed by the genetically modified cell,
   (ii) determining baseline rhythm of the cardiac syncytial cell in vitro;
   (iii) contacting the cardiac syncytial cell with the genetically modified cell in vitro;
   (iv) determining the rhythm of the cardiac syncytial cell in vitro following the contacting step of (iii); and
   (v) comparing the baseline rhythm of step (ii) to the rhythm of step (iv), wherein the coupling of the cardiac syncytial cell and the genetically modified cell is indicated when the rhythm of step (ii) differs from the rhythm of step (iv).

16. The method of claim 15, wherein the gene is a gene encoding a hyperpolarization-activated, cyclic nucleotide-gated 2 (HCN2) channel.

17. The method of claim 15, wherein rhythm is determined by photodiode detection of dye administered to the first and second cardiac syncytial cells.

18. The method of claim 17, wherein the dye is a Ca-sensitive dye.

19. The method of claim 18, wherein the Ca-sensitive dye is fluo-3.

20. The method of claim 17, wherein the dye is a voltage sensitive dye.

21. The method of claim 15, wherein rhythm is determined by edge detection in said first and second cardiac syncytial cells.

22. The method of claim 15, wherein rhythm is determined with electrodes embedded in a test well.

23. The method of claim 22, wherein the electrodes comprise one 150×30 micrometer diameter stimulating electrode and one 30 micrometer diameter electrode.

24. The method of claim 23, wherein the testing well has an inner diameter of at least 3 mm by 3 mm.

25. The method of claim 15, wherein rhythm is determined with a glass patch electrode in a testing well.

26. The method of claim 25, wherein the testing well has an inner diameter of at least 3 mm by 3 mm.

\* \* \* \* \*

UNITED STATES PATENT AND TRADEMARK OFFICE
CERTIFICATE OF CORRECTION

| | | |
|---|---|---|
| PATENT NO. | : 8,192,929 B2 | Page 1 of 1 |
| APPLICATION NO. | : 11/792426 | |
| DATED | : June 5, 2012 | |
| INVENTOR(S) | : Robinson et al. | |

It is certified that error appears in the above-identified patent and that said Letters Patent is hereby corrected as shown below:

On column one, lines 18-20 replace text with the following:

This invention was made with government support under Grant No. HL-28958 awarded by National Institutes of Health. The government has certain rights in the invention.

Signed and Sealed this
Eighth Day of January, 2013

David J. Kappos
*Director of the United States Patent and Trademark Office*